United States Patent [19]
Rousset

[11] Patent Number: 5,466,782
[45] Date of Patent: Nov. 14, 1995

[54] METHOD FOR SEPARATING A COMPOUND CONTAINING GLYCOLIPIDS, LYSOPHOSPHOLIPIDS, SPHINGOLIPIDS AND CERAMIDES OF PLANT ORIGIN

[75] Inventor: Gerard Rousset, Wissous, France

[73] Assignee: Laboratoires Inocosm, Chatenay Malabry, France

[21] Appl. No.: 150,150

[22] PCT Filed: Feb. 27, 1992

[86] PCT No.: PCT/FR92/00182

§ 371 Date: Apr. 22, 1994

§ 102(e) Date: Apr. 22, 1994

[87] PCT Pub. No.: WO92/21321

PCT Pub. Date: Dec. 10, 1992

[30] Foreign Application Priority Data

May 27, 1991 [FR] France ................... 91 06336

[51] Int. Cl.⁶ .................. A61K 7/48; C07H 1/08; C07K 14/415; C11B 1/10
[52] U.S. Cl. ............ 530/374; 530/375; 536/18.5; 536/55.3; 536/128; 554/13; 554/14; 554/21
[58] Field of Search .................. 530/374, 375, 530/412, 423, 424, 427; 424/401, 195.1; 536/18.5, 55.3, 128; 514/2, 25, 42, 143, 144, 613, 783, 785, 847; 554/14, 14, 21

[56] References Cited

U.S. PATENT DOCUMENTS

| | | | |
|---|---|---|---|
| 2,377,291 | 5/1945 | Coleman | 530/374 |
| 4,745,186 | 5/1988 | Mudd et al. | 424/195.1 |
| 5,026,548 | 6/1991 | Evans et al. | 424/195.1 |
| 5,215,759 | 6/1993 | Mausner | 424/457 |

FOREIGN PATENT DOCUMENTS

| | | |
|---|---|---|
| 0278505 | 8/1988 | European Pat. Off. . |
| 2379282 | 9/1978 | France . |
| 2400552 | 3/1979 | France . |
| 1497 | 1/1984 | Japan ................... 530/374 |
| 1323330 | 7/1973 | United Kingdom . |
| WO84/01710 | 5/1984 | WIPO . |
| WO86/01713 | 3/1986 | WIPO . |
| WO90/05521 | 5/1990 | WIPO . |

OTHER PUBLICATIONS

Patent Abstracts of Japan, vol. 12, No. 37 (C–473) 1988, and JP A, 62187404 (Shibamoto Takeshi) 1987.

Masao Ohnishi et al., "Sphingolipid classes and their molecular species in wheat flour", Agricultural and Biological Chemistry, vol. 49, No. 12, pp. 3609–3611, 1985.

Osagie et al., A.U. "Lipid composition of millet seeds", Lipids, vol. 19, No. 12, pp. 858–965, 1984.

M. J. L. Lin et al., "Hard red spring and durum wheat polar lipids. I. Isolation and quantitative determinations", Cereal Chemistry, vol. 51, No. 1, pp. 17–33, 1974.

World Patents Index Latest, Section Ch, Week 8407, Derwent Publ. Ltd., Class D, AN 84–039643 and JP A, 59001497, 1984.

H. Wieser et al., "Characterization of ethanol–extractable reduced subunits of glutenin separated by reversed–phase high–performance liquid chromatography", Journal of Cereal Science, vol. 12, pp. 63–71, 190.

*Primary Examiner*—Jeffrey E. Russel
*Attorney, Agent, or Firm*—Wolf, Greenfield & Sacks

[57] ABSTRACT

A method for separating a composition containing glycolipids, lysopholipids, sphingolipids and ceramides of plant origin is described. A liquid alcohol is heated to a temperature of between 50° and 80° C., a plant composition or plant extract is introduced into the alcohol to form a mixture, the mixture is hot-filtered so as to separate the filtrate from a dilapidated filter cake, and the alcohol is evaporated from the filtrate such that a lipid residue which contains glycolipids, lysophospholipids, sphingolipids, and ceramides is obtained. The lipid residue can be used in cosmetology or dermatology.

14 Claims, No Drawings

METHOD FOR SEPARATING A COMPOUND CONTAINING GLYCOLIPIDS, LYSOPHOSPHOLIPIDS, SPHINGOLIPIDS AND CERAMIDES OF PLANT ORIGIN

The present invention relates to a method for separating a compound containing glycolipids, lysophospholipids, sphingolipids and ceramides of plant origin.

The hydration of the skin is one of the greatest problems facing specialists in cosmetology: it is well known that water is a vital component of the human organism; its concentration, which amounts to 60 to 70% in the dermis, drops to 12% in the stratum corneum, i.e. the upper layers of the epidermis.

In order for the skin to preserve its suppleness and elasticity and to prevent the premature formation of lines or small wrinkles, it is essential to maintain this water content, preventing any dehydration following cutaneous evaporation or sweating.

In order to overcome the consequences of the above-mentioned phenomena and to delay the ageing of the skin as much as possible, cosmetology specialists have developed various compositions for reestablishing the water content of the upper layers of the epidermis either by retarding their dehydration or by encouraging their rehydration.

The first of these compositions, proposed at the beginning of the Sixties, were creams based on Vaseline or beeswax which where not always very well accepted by consumers in view of their greasy and oily nature.

In order to overcome this disadvantage, compositions in the form of emulsions consisting of a mixture of water and oil and having the advantage of being far more pleasant to use were developed.

In addition to these compositions, which in principle act by providing the skin with the lipids which they tend to lack, more sophisticated hydrating products appeared which comprise, as active agents, moistening or hygroscopic components which, by affinity, can take up and retain the surrounding water so as to maintain a moist atmosphere about the cells and on the surface of the skin. Lanoline, soya lecithins, glycerol, mucopolysaccharides or even allantoin derivatives can be cited among these active components.

In addition to these wetting or hygroscopic agents, the hydrating compositions currently offered to consumers very often contain so-called "natural moisturising factors" which are normally present in the epidermis and of which a lack has been noted in subjects with dehydrated skin or skin which tends to be dry. These products, of which the activity has been noted in the skin hydration mechanisms, are, for example, amino acids (serine, lysine, tyrosine, etc.), urea, sodium, potassium, carboxylic pyrrolydonic acid, etc.

Even more recently, the role played in the skin hydration mechanisms by phospholipids, and in particular ceramides, which are also normally present in the corneous layer, has come to the fore. It has been possible to demonstrate that these products act like cement between the bricks of the cells and thus help to improve water retention and the skin's resistance to external aggression.

There are currently available on the cosmetic market hydrating compositions (in the form of creams, gels or solutions) which contain ceramides associated with texture agents enabling the intercellular tissue to be "concreted" and which have proved to be particularly efficient and have consequently been well received by consumers.

However, the ceramides present in these compositions have the disadvantage of being of animal origin and extracted from the brain or nerve tissue of animals.

This disadvantage might be such that it could slow down or even completely halt future development of hydrating products based on ceramides, given that, for ecological reasons, it is currently sought to protect animals as much as possible and to avoid using them as far as possible in the laboratory. Encouraged by the various animal-protection organisations, this current tendency is such that products of animal origin are increasingly unacceptable.

Independently of these concerns of a philosophical kind, the principal reason for which the development of products, in particular cosmetic products from the animal kingdom, might be delayed in future, is connected with the appearance in ruminants of new viruses of the prion type which develop in the brain and nerve tissue and which are, in particular, responsible for the illness known as "mad cow disease". These viruses currently appear to be mutating, and the possibility of their spreading and developing in humans, which would have dramatic consequences, is not ruled out.

The above risk might cause researchers to change their opinion, resulting in an increased use of the plant kingdom or products of a marine origin to replace animal products, despite the increased difficulties associated with the fact that animal products are already in a partially or totally synthesised state whilst the use of plant products still requires additional operations which can prove to be lengthy and expensive.

The subject of the present invention, which is within the above context, is a method for separating a composition containing glycolipids, lysophospholipids, sphingolipids and ceramides of plant origin, which can then be used for manufacturing hydrating cosmetological compositions, and which is thus such that it can overcome the disadvantages posed by the presence of ceramides extracted from animal brains or nerve cells in compositions of this type.

To this end, it should be noted that it is known, in particular from the document *AGRICULTURAL AND BIOLOGICAL CHEMISTRY*, vol. 49, no. 12, 1985, TOKYO JP, pages 3609–3611, that glycosal-ceramides and ceramides are present in certain plant compounds, such as wheat flour.

The method according to the invention is characterised in that a given amount of a liquid alcohol, in particular methanol or ethanol, is heated to a temperature of between 50° and 80° C., a plant compound, such as cereal flour or an extract such as bran or lipids extracted from cereals by chlorinated solvents, such as methylene chloride or chloroform, is introduced into the alcohol under intensive stirring, stirring is continued, and the mixture is left to stand whilst the temperature is maintained, it is then hot-filtered so as to separate a filtrate from a delipidated filter cake, and the alcohol is evaporated from the filtrate such that a residue containing glycolipids, lysophospholipids, sphingolipids and ceramides of plant origin is obtained.

By way of example, satisfactory results have been obtained by continuing stirring for 30 minutes after the plant compound has been introduced and then leaving the mixture to stand for one hour.

The alcohol used can be any liquid alcohol but legislation concerning the area of cosmetology requires a denaturated alcohol to be used. For reasons of manufacturing costs, it is advantageous to recycle the alcohol which has already been used for one or more extractions.

The plant product most frequently used in accordance with the invention is, nevertheless, whole wheat flour, both for reasons of manufacturing costs and for performance.

The amount of whole wheat flour to be added is approximately 50 weight % of the amount of alcohol initially used.

It should be noted that extraction using hot alcohol enables both the triglycerides (phospholipids, glycolipids and ceramides) to be solubilised and the ceramides to be purified since they are practically alone in precipitating in alcohol at low temperature.

According to a first variant of the invention, the alcohol is evaporated from the filtrate using a flask immersed in particular in an oil bath. This is, as it were, an alembic-type reactor. It is thus possible to recover at the bottom of the flask a pasty residue which is homogeneous to a greater or lesser extent and which contains 3 to 6% of ceramides.

The performance of this method involves a relatively lengthy and awkward operation which a second, "more refined" variant of the invention overcomes.

According to this variant, the lipid-rich filtrate separated from the delipidated filter cake is cooled to a temperature of between −20° and +4° C. such that selective precipitation of a ceramide-containing mixture is obtained, the product is then filtered for a second time, whilst the temperature is maintained, such that a product containing ceramides and alcohol is obtained, the product is then left to return to ambient temperature such that the ceramides are separated from the alcohol and the residual alcohol is evaporated.

It is advisable to subject the lipid paste containing the ceramides to an additional treatment, for example washing with acetone or evaporation in the oven to remove the remaining alcohol. A lipid powder containing 80 to 90% of ceramides, 10 to 20% of phospholipids and 10 to 20% of glycolipids can thus be recovered at the end of the process. This powder can be transferred as it is to a dermatological or cosmetological laboratory for the manufacture of a hydrating composition, or it can be dried and pulverised in a manner known per se, so as to obtain 5 to 15 g of powder per kilogram of flour used. A powder of this type has the advantage of being particularly stable, which allows it to be packaged directly, in particular in aluminium sachets, without requiring the addition of preservatives. It can also be placed in an aqueous or oily solution.

The following step of this method consists in treating the filtrate obtained at the end of the second filtration and advantageously containing 50% of triglycerides, 25% of phospholipids and 25% of glycolipids.

To this end, the alcohol is evaporated in a manner known per se and the triglycerides are solubilised with acetone such that a powder advantageously containing 50% of glycolipids, 25% of phospholipids and 25% of lysophospholipids is obtained. The glycolipids can be used in dermatology or cosmetology as hydrating agents and the phospholipids and lysophospholipids can be used as emulsifiers, as vectors of active constituents, and as liposome components, lysophospholipids being better emulsifiers than phospholipids.

It should be noted that wheat is particularly rich in lysophospholipids.

The invention also relates to the use in the area of cosmetology or dermatology of the product of plant origin containing a lipid mixture comprising glycolipids, lysophospholipids, sphingolipids and ceramides of plant origin, as obtained by the above method.

It should be noted that it is possible to introduce a product of this type into liposomes.

Cosmetic products of plant origin containing sphingolipids have already been proposed in the document PATENT ABSTRACTS OF JAPAN, vol. 12, no. 37 (C-473), Feb. 4, 1988. However, these cosmetic products contained neither glycolipids, lysophospholipids, nor ceramides.

In accordance with the invention, it is also sought to profit from the delipidated filter cake obtained at the end of the first filtration for the manufacture of various cosmetic or dermatological products.

One of the possibilities offered in this respect consists in preparing plant gliadin. Gliadin is a plant protein which is soluble in hydroalcoholic solutions with the result that it is particularly advantageous in dermatology or cosmetology.

To this end, and according to a further characteristic of the invention, 20 to 40 weight % of demineralised water is added to this cake, the resultant paste is stirred at ampient temperature, and it is left to decant for several days, the plant gliadin-rich fraction floating on the surface is recovered, and it is subjected to filtration on filter paper such that a paste containing plant gliadin which can be used in cosmetology is recovered on this paper.

By way of example, satisfactory results have been obtained by the continued stirring of the paste for one hour at ambient temperature and leaving it to decant for 3 days.

The product containing plant gliadin obtained by the above method can be added to alcoholic products to prevent irritation and avoid the appearance of characteristic redness on the users' faces. It can also be used as a hydrating agent in hydroalcoholic media.

When the gliadin has been extracted, the remaining cake can be used for the manufacture of a cosmetic product rich in native proteins of the type which are known and generally marketed under the name of "tensing agents" and which are generally used for cleansing the skin.

According to a further characteristic of the invention, to manufacture a tensing agent of this type, the above-mentioned delipidated filter cake is recovered, it is introduced into a mixture of demineralised water, 0.9 to 3% of sodium chloride and, optionally, preservatives, the resultant paste is stirred, and it is left to decant for approximately twelve hours at ambient temperature, the protein-containing fraction floating on the surface is recovered, it is heated to a temperature of between 40° and 50° C., and it is subjected to at least one filtration on a filter paper such that a paste containing proteins constituting the plant tensing agent is recovered on this paper.

By way of example, satisfactory results have been obtained by the introduction of the delipidated filter cake into the above mixture in a proportion of 50 weight % and stirring the resultant paste for one hour.

Before this treatment is performed, it is advantageous for the cake to be subjected to a preliminary washing process using pure water to avoid the presence of alcohol as far as possible in the remainder of the process.

A mixture of phenoxyethanol, citric acid and sodium methyl parahydroxybenzoate, i.e. three preservatives approved at international level, can be used as the preservative. It should be noted that the presence of these preservatives is unnecessary when the plant tensing agent is intended to be highly diluted for its use. By way of example, interesting results have been obtained by the addition of approximately 0.6% of phenoxyethanol, 0.6% of citric acid and 0.4% of sodium methyl parahydroxybenzoate to the initial salt water.

According to a further characteristic of the invention, the protein-containing fraction floating on the surface is subjected to a first filtration at a temperature of between 40° and 50° C., it is left to cool in ambient air for approximately twelve hours, and it is then subjected to a second filtration at ambient temperature.

Advantageously, 1% to 5% of activated carbon (in particular the product marketed by MERCK under the name of CLAROCARBONE), which acts as a bleaching agent and deodorant, is added to the mixture before it is heated to between 40° and 50° C.

The plant tensing agent obtained by the above method can be used in the area of cosmetology or dermatology, diluted to different strengths.

When it is highly diluted (0.2/0.3% of protein), it can constitute a skin-cleansing product with high tolerance which can be used without the need for rinsing; a product of this type is particularly advantageous for cleansing skins suffering from acne, psoriasis, eczema, etc.

In a concentration of approximately 6% of proteins, this product can be used to manufacture creams of the type which "draw" the skin. It then has a tensing ability comparable to that of bovine or horse serum.

In this concentration, a product is obtained which is comparable to those used to erase wrinkles and give a burst of radiance.

It should also be noted that, in a concentration of the order of 10% of proteins, this product can be used in bust-firming compositions.

Consequently, the invention also enables a plant tensing agent which can give rise to various applications and is in the form of a solution, a cream or a gel, to be obtained.

I claim:

1. Method for separating a composition containing glycolipids, lysophospholipids, sphingolipids and ceramides of plant origin, characterized in that a liquid alcohol is heated to a temperature of between 50° and 80° C., a plant composition or a plant extract is introduced into the alcohol under intensive stirring to form a mixture, stirring is continued, and the mixture is left to stand whilst the temperature is maintained, then it is hot-filtered so as to separate a filtrate from a dilapidated filter cake and the alcohol is evaporated from the filtrate such that a lipid residue which contains glycolipids, lysophospholipids, sphingolipids and ceramides of plant origin and which can be used in cosmetology or dermatology is obtained.

2. Method according to claim 1, characterized in that 50 weight % of whole wheat flour is introduced into the liquid alcohol that has been heated to a temperature of between 50° and 80° C.

3. Method according to claim 1, characterized in that the alcohol is evaporated from the filtrate using a flask immersed in an oil bath such that a pasty residue which contains 3 to 6 weight % of ceramides is recovered at the bottom of the flask.

4. Method according to claim 1, characterized in that the filtrate containing the lipids and separated from the dilapidated filter cake is cooled to a temperature of between −20° and +4° C. such that a ceramide-containing mixture is precipitated, the product is then filtered for a second time whilst the temperature is maintained in order to recover a ceramide-containing product, the product is then left to return to ambient temperature so as to separate the ceramides from the alcohol, the residual alcohol is evaporated, and a lipid powder containing 80–90 weight % of ceramides is recovered.

5. Method according to claim 4, characterized in that the filtrate which is obtained at the end of the second filtration and which contains 50 weight % triglycerides, 25 weight % phospholipids and 25 weight % glycolipids is recovered, the residual alcohol is evaporated, and the triglycerides are solubilized with acetone such that a powder containing 50 weight % glycolipids, 25 weight % phospholipids and 25 weight % lysophospholipids and which can be used in dermatology or cosmetology is obtained.

6. Method according to claim 1, characterised in that the delipidated filter cake obtained at the end of the first filtration is recovered, 20 to 40 weight % of demineralised water is added to this cake, the resultant paste is stirred at ambient temperature, and it is left to decant for several days, the fraction floating on the surface containing plant gliadin is recovered and is subjected to filtration on a filter paper such that a paste which contains plant gliadin and which can be used in cosmetology or in dermatology is recovered on this paper.

7. Method according to claim 6, characterized in that the filter cake remaining after the gliadin is recovered, is introduced into a mixture of demineralized water, 0.9 to 3 weight % sodium chloride and, optionally, preservatives, the resultant paste is stirred and it is left to decant for approximately twelve hours at ambient temperature, the fraction floating on the surface is recovered, this floating fraction is heated to a temperature of between 40° and 50° C. and is subjected to at least one filtration on a filter paper such that a paste which contains native proteins and which can be used as a tensing agent in dermatology or cosmetology is recovered on this paper.

8. Method according to claim 7, characterized in that the fraction floating on the surface is subjected to a first filtration at a temperature between 40° and 50° C., the fraction is left to cool in ambient air for approximately twelve hours, and the fraction is subjected to a second filtration at ambient temperature.

9. The lipid residue obtained by the method of claim 1 having glycolipids, lysophospholipids, sphingolipids and ceramides of plant origin for use in the area of cosmetology or dermatology.

10. Method according to claim 1 wherein the liquid alcohol is selected from the group consisting of methanol and ethanol.

11. Method according to claim 1 wherein the plant composition that is introduced into the alcohol is cereal flour.

12. Method according to claim 1 wherein the plant extract is extracted from a cereal.

13. Method according to claim 1 wherein the plant extract is selected from the group consisting of bran and lipids extracted from cereals.

14. Method according to claim 1 wherein the plant extract is extracted using a chlorinated solvent selected from the group consisting of methylene chloride and chlorine.

* * * * *